(12) United States Patent
Mansholt et al.

(10) Patent No.: US 12,144,588 B2
(45) Date of Patent: Nov. 19, 2024

(54) COMBINED CORE TEMPERATURE AND SKIN TEMPERATURE SENSOR

(71) Applicant: Solventrum Intellectual Properties Company, Maplewood, MN (US)

(72) Inventors: Michael W. Mansholt, Cologne (DE); Henning Reuter, Willich (DE)

(73) Assignee: SOLVENTUM INTELLECTUAL PROPERTIES COMPANY, Maplewood, MN (US)

( * ) Notice: Subject to any disclaimer, the term of this patent is extended or adjusted under 35 U.S.C. 154(b) by 881 days.

(21) Appl. No.: 15/733,785

(22) PCT Filed: Apr. 29, 2019

(86) PCT No.: PCT/IB2019/053485
§ 371 (c)(1),
(2) Date: Oct. 26, 2020

(87) PCT Pub. No.: WO2019/211720
PCT Pub. Date: Nov. 7, 2019

(65) Prior Publication Data
US 2021/0244285 A1 Aug. 12, 2021

Related U.S. Application Data

(60) Provisional application No. 62/665,873, filed on May 2, 2018.

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/6833* (2013.01); *G01K 1/165* (2013.01); *G01K 13/20* (2021.01);
(Continued)

(58) Field of Classification Search
CPC . A61B 5/01; A61B 5/6833; A61B 2562/0271; A61B 2562/164; G01K 13/20; G01K 1/165
See application file for complete search history.

(56) References Cited

U.S. PATENT DOCUMENTS

2010/0268114 A1* 10/2010 Van Duren .......... A61B 5/6833
600/549
2013/0085708 A1 4/2013 Sattler
2013/0317388 A1* 11/2013 Bieberich .............. G01K 17/00
600/549

FOREIGN PATENT DOCUMENTS

CN 101112306 1/2008
EP 1768546 4/2007
(Continued)

OTHER PUBLICATIONS

International Search Report for PCT International Application No. PCT/IB2019/053485, mailed on Sep. 9, 2019, 4 pages.

*Primary Examiner* — Devin B Henson
*Assistant Examiner* — Jonathan M Haney
(74) *Attorney, Agent, or Firm* — Vorys, Sater, Seymour and Pease LLP

(57) ABSTRACT

Aspects of the present disclosure relate to a temperature device having a flexible substrate; and an electrical circuit on a surface of the flexible substrate. The electrical circuit includes at least three thermal sensors including at least one skin thermal sensor, a plurality of electrical pads, a plurality of conductive traces connecting the at least three thermal sensors with the plurality of electrical pads.

9 Claims, 13 Drawing Sheets

(51) Int. Cl.
*G01K 1/16* (2006.01)
*G01K 13/20* (2021.01)

(52) U.S. Cl.
CPC . *A61B 2562/0271* (2013.01); *A61B 2562/164* (2013.01)

(56) References Cited

FOREIGN PATENT DOCUMENTS

| | | |
|---|---|---|
| JP | 2012073127 | 4/2012 |
| WO | WO 2012-112222 | 8/2012 |
| WO | WO 2014-161634 | 10/2014 |
| WO | WO 2015-025311 | 2/2015 |
| WO | WO 2015-092627 | 6/2015 |
| WO | WO 2016-016792 | 2/2016 |

\* cited by examiner

COMBINED CORE TEMPERATURE AND SKIN TEMPERATURE SENSOR

CROSS REFERENCE TO RELATED APPLICATIONS

This application is a national stage filing under 35 U.S.C. 371 of PCT/IB2019/053485, filed Apr. 29, 2019, which claims the benefit of U.S. Provisional Patent Application No. 62/665,873, filed May 2, 2018, the disclosures of which are incorporated by reference in their entirety herein.

BACKGROUND

The subject matter relates to a device for use in the estimation of deep tissue temperature (DTT) as an indication of the core temperature of humans or animals.

Deep tissue temperature measurement is the measurement of the temperature of organs that occupy cavities of human and animal bodies (core temperature). DTT measurement is desirable for many reasons. For example, maintenance of core temperature in a normothermic range during the perioperative cycle has been shown to reduce the incidence of surgical site infection; and so, it is beneficial to monitor a patient's core temperature before, during, and after surgery. Of course, noninvasive measurement is highly desirable, for the safety and the comfort of a patient, and for the convenience of the clinician. Thus, it is most advantageous to obtain a noninvasive DTT measurement by way of a device placed on the skin.

SUMMARY

Aspects of the present disclosure relate to a temperature device having a flexible substrate; and an electrical circuit on a surface of the flexible substrate. The electrical circuit includes at least three thermal sensors including at least one skin thermal sensor, a plurality of electrical pads, a plurality of conductive traces connecting the at least three thermal sensors with the plurality of electrical pads.

It is desirable that zero heat flux, deep tissue temperature measurement device constructions be disposable. Thus, the constructions should be easy and inexpensive to fabricate and assemble, have a low mass and a low profile, and comprise inexpensive materials and parts. It is particularly desirable that disposable DTT measurement device constructions be assembled from low-profile, light weight, flexible assemblies that enable zero heat flux temperature measurement at various locations on a human or animal body.

A temperature device for zero heat flux deep tissue temperature measurement includes a flexible substrate with at least two thermal sensors disposed in a spaced-apart relationship and separated by one or more flexible layers of thermally insulating material. Preferably the sensors are maintained in a spaced-apart relationship by a flexible thermal (and electrical) insulator. The substrate supports at least the thermal sensors, the separating thermal insulator, and a heater.

Although temperature device constructions are described in terms of preferred embodiments comprising representative elements, the embodiments are merely illustrative. It is possible that other embodiments will include more elements, or fewer, than described. It is also possible that some of the described elements will be deleted, and/or other elements that are not described will be added. Further, elements may be combined with other elements, and/or partitioned into additional elements.

DETAILED DESCRIPTION

Aspects of the present disclosure relate to a temperature monitoring device useful in measuring core temperatures and skin temperatures of a patient. Further aspects of the present disclosure relate to a system for controlling heat energy transfer to a patient from a warming device based on core temperatures and skin temperature of the patient.

Temperature monitoring devices can be useful in measuring core temperatures. The temperature monitoring device can have a thermal sensor useful in monitoring a temperature indicative of a core temperature and a thermal sensor useful in monitoring a temperature indicative of a skin temperature of a patient. Core temperature devices can be either invasive (such as esophageal or rectal thermometers) or non-invasive (which do not need to be inserted into any portion of the body). In at least one embodiment, the core temperature can be determined from a plurality of thermal sensors placed in multiple configurations and without the use of heaters (i.e., an unheated core temperature device). An unheated temperature device can differ from the zero-heat flux temperature device in that the zero-heat flux device uses a heater and the unheated temperature device may use a thermal-equilibrium method. Aspects of the present disclosure relate to a core temperature device that is either unheated or heated (e.g., zero-heat flux).

Figure 1:
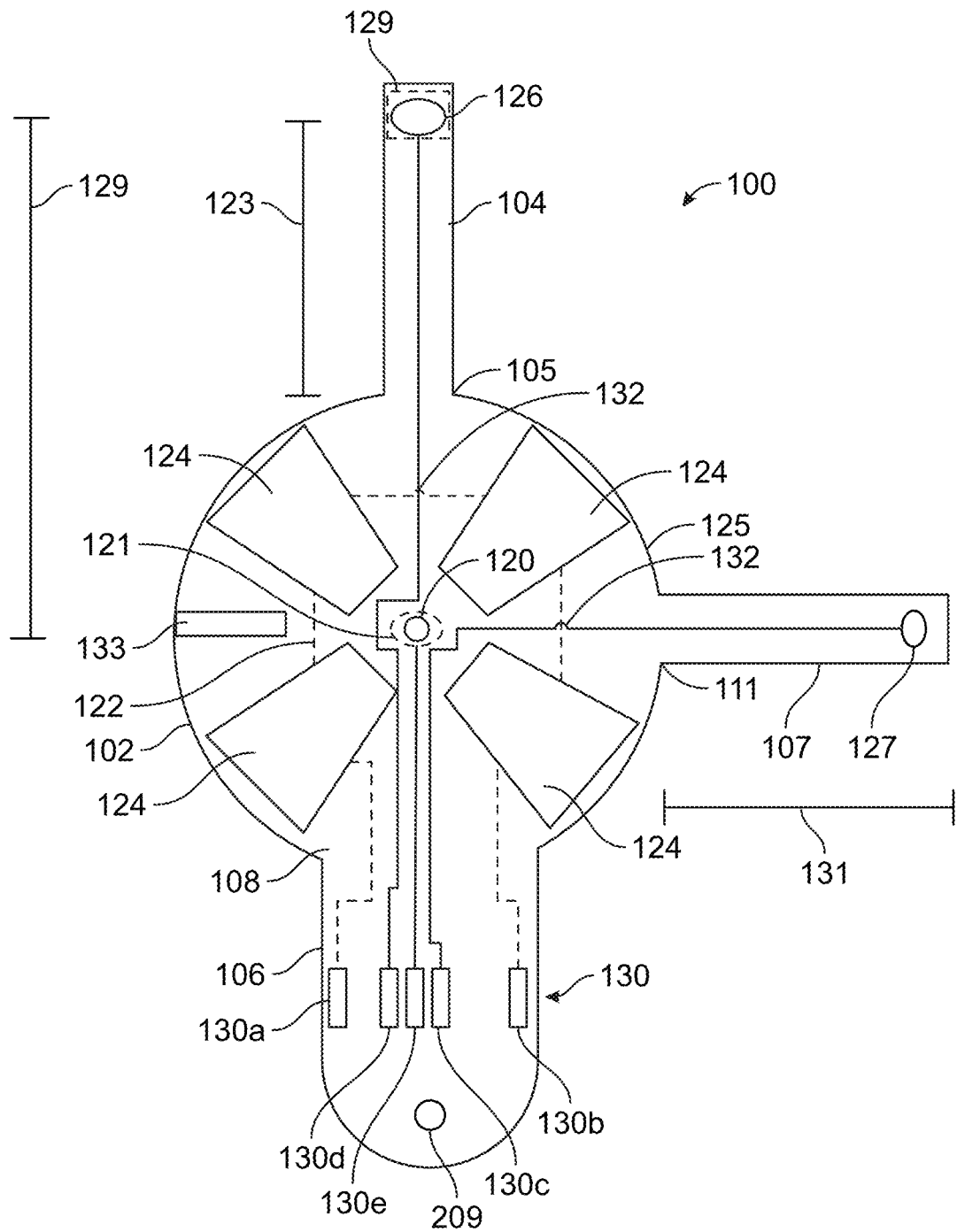
FIG. 1 is a plan view of a side of a flexible substrate showing an electrical circuit disposed on a surface of the substrate for temperature measurement, according to aspects of the present disclosure.
Figure 2:
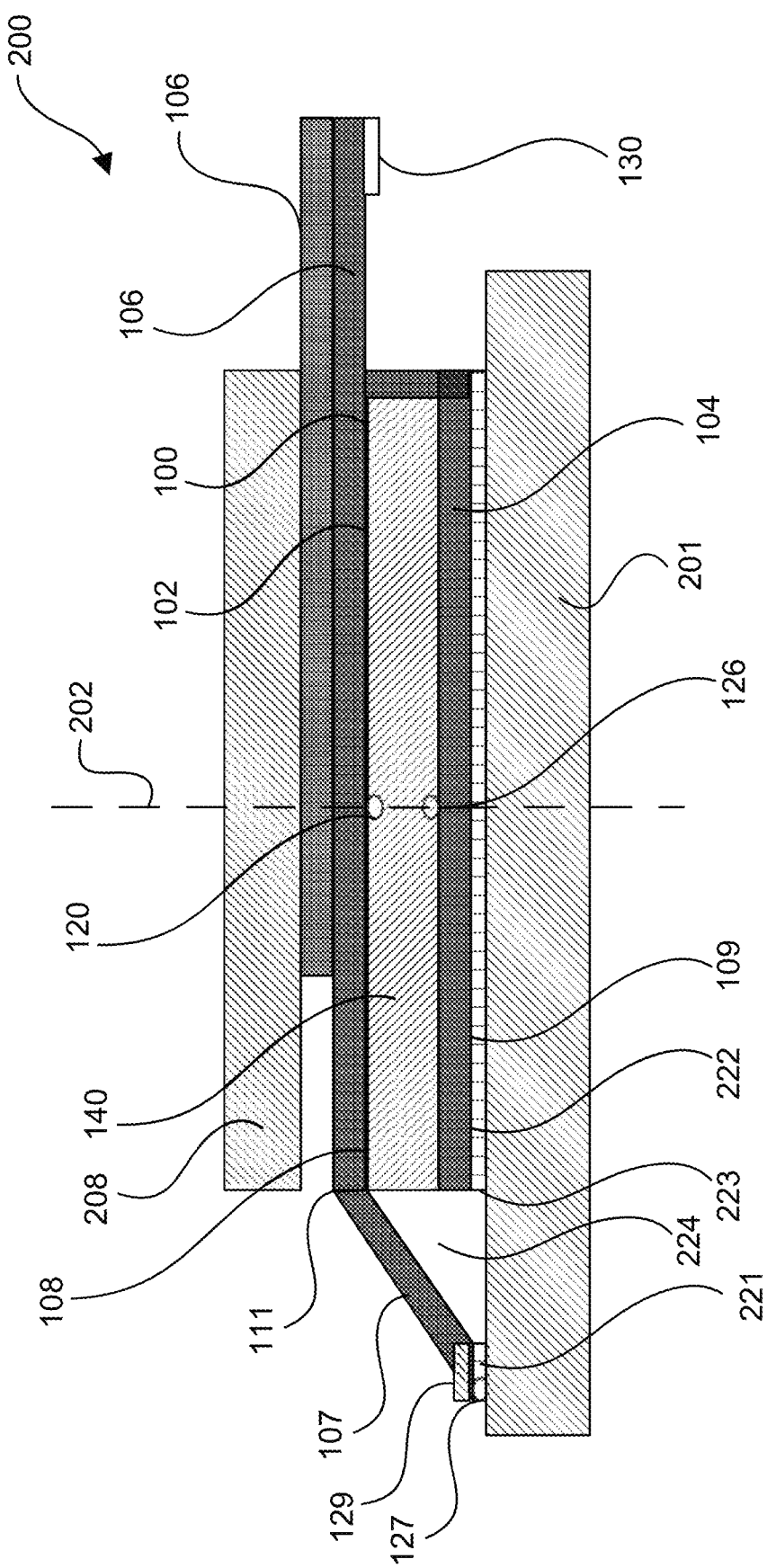
FIG. 2 is a side sectional view of a temperature device that incorporates the electrical circuit of FIG. 1, according to aspects of the present disclosure.
Figure 3:
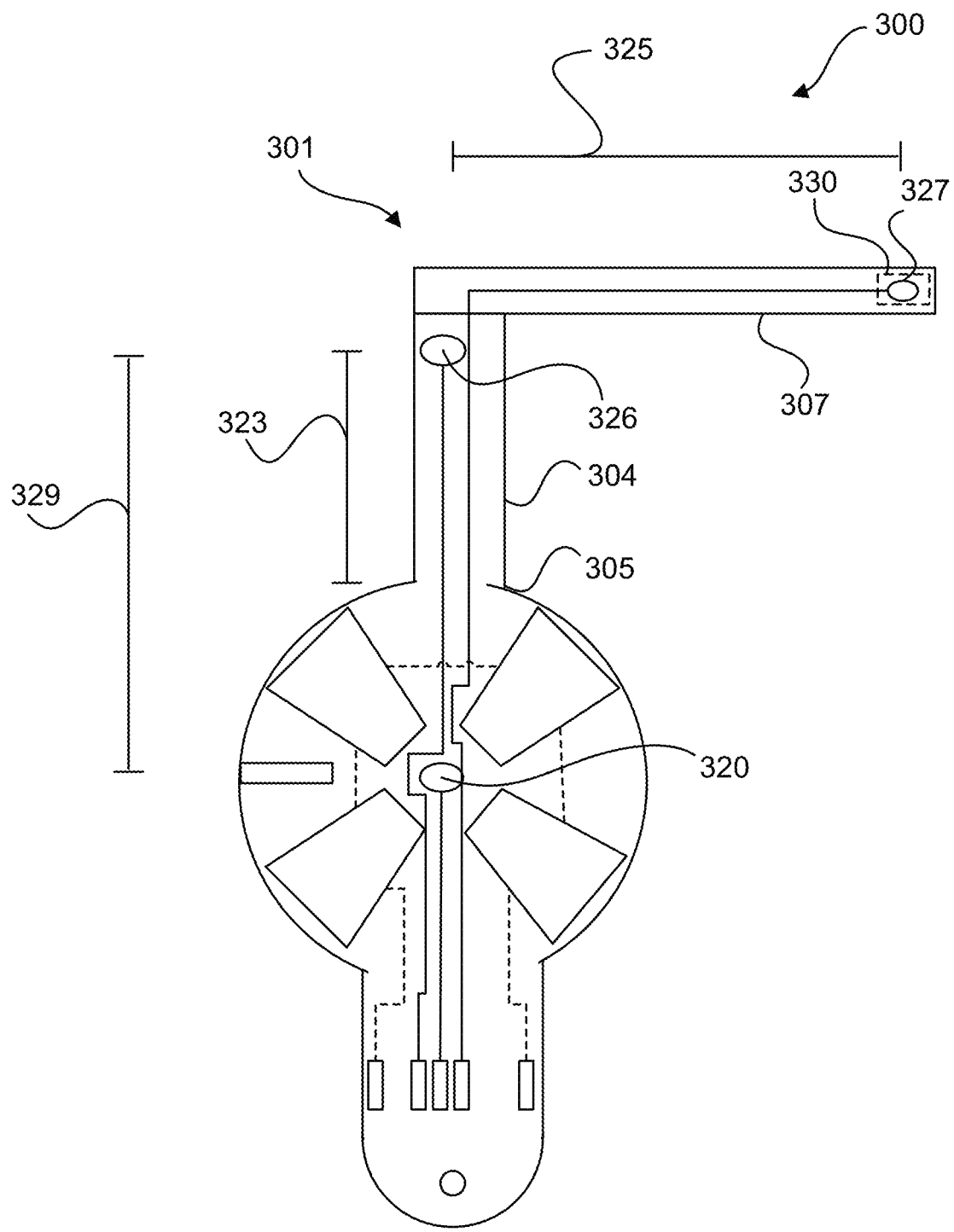
FIG. 3 is a plan view of a side of a flexible substrate showing an electrical circuit disposed on a surface of the substrate for temperature measurement, according to aspects of the present disclosure.
Figure 4:
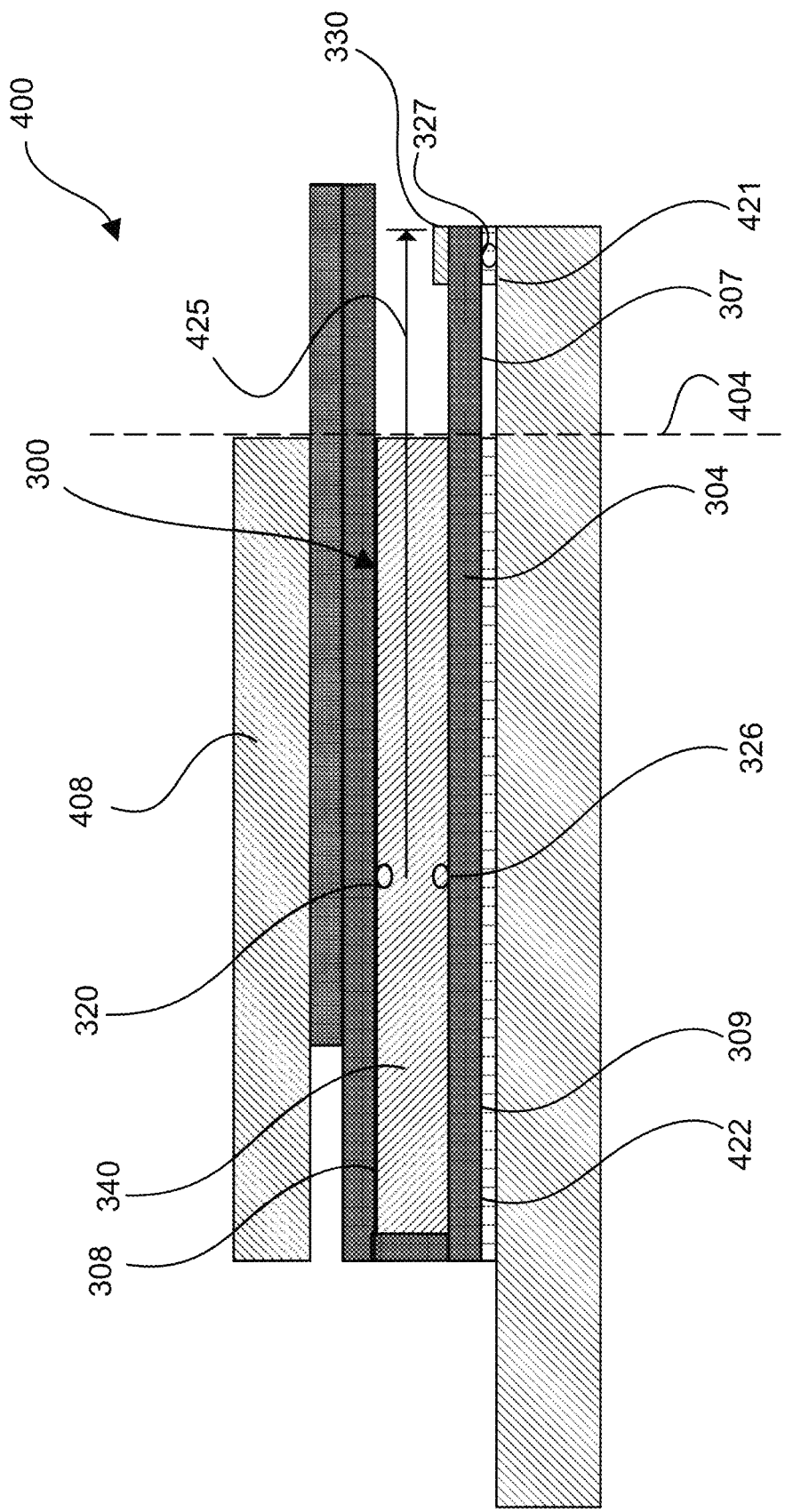
FIG. 4 is a side sectional view of a temperature device that incorporates the electrical circuit of FIG. 3, according to aspects of the present disclosure.

An inexpensive, disposable, zero-heat-flux DTT measurement device is described and claimed in the priority application and illustrated in FIGS. 1 thru 4. The device is constituted of a flexible substrate and an electrical circuit disposed on a surface of the flexible substrate. The electrical circuit includes an essentially planar heater which is defined by an electrically conductive copper trace and which surrounds an unheated zone of the surface, a first thermal sensor disposed in the zone, a second and third thermal sensor disposed outside of the heater trace, a plurality of electrical pads disposed outside of the heater trace, and a plurality of conductive traces connecting the first, second and third thermal sensors and the heater trace with the plurality of electrical pads. Sections of the flexible substrate are folded together to place the first and second thermal sensors in proximity to each other. A layer of insulation disposed between the sections separates the first and second thermal sensors. The device is oriented for operation so as to position the heater and the first thermal sensor on one side of the layer of insulation and the second thermal sensor on the other and in close proximity to an area of skin where a measurement is to be taken and a third thermal sensor not proximate to the heater to measure a skin temperature. As seen in FIGS. 2 and 4, the layout of the electrical circuit on a surface of the flexible substrate provides a low-profile, zero-heat-flux DTT measurement device that is essentially planar, even when the sections are folded together.

Design and manufacturing choices made with respect to a zero-heat-flux DTT measurement device can influence the operation of the device. One such design choice relates to the thermal sensors used in the detection of the zero-heat-flux condition. Given the importance of core temperature, it is very desirable that the thermal sensors produce accurate temperature data in order to enable reliable detection of the zero-heat-flux condition and accurate estimation of core temperature. The tradeoff is between accuracy and cost of the thermal sensor. A number of thermal sensor devices are candidates for use in zero-heat-flux DTT measurement. Such devices include PN junctions, thermocouples, resistive temperature devices, and thermistors, for example. Thermistors are a good choice for reasons of small size, handling convenience, ease of use, and reliability in the temperature range of interest. Their relatively low cost makes them desirable candidates for single-use, disposable temperature measurement devices.

The magnitude of a thermistor's resistance changes in response to a change of the temperature of the thermistor. Thus, to determine the magnitude of the temperature, the thermistor's resistance is measured and converted to a temperature value using a known relationship. However, batch-to-batch manufacturing variances can yield a large range variance in thermistor resistance. For example, low-cost thermistors can exhibit a range of ±5% in resistance values from device to device at a given temperature, which yields a range of +2.5° C. in temperature. Such a large range in variance can compromise the accuracy and reliability of zero-heat-flux temperature measurement. Thus, while it is desirable to use such thermistors in order to limit the cost of parts and labor in manufacturing zero-heat-flux DTT measurement devices, it is important to reduce, if not remove, the effects of resistance variance on device operation.

The range of thermistor resistance variance can be neutralized by calibration of thermistor resistance using known methods, such as the Steinhart-Hart equation, which require knowledge of coefficients derived from values of thermistor resistance measured at fixed temperatures. When a thermistor is operated, the coefficients are used in known formulas to correct or adjust the magnitude of its indicated resistance. Such correction is called calibration.

FIG. 1 illustrates a layout of an electrical circuit for a temperature measurement device. The electrical circuit is disposed on a flexible substrate to adapt or conform the physical configuration of the temperature measurement device to differing contours encountered at different temperature measurement locations. Preferably, but not necessarily, the flexible substrate is constructed or fabricated to have a plurality of contiguous sections. For example, the flexible substrate 100 has four contiguous sections 102, 104, 106, and 107. The first, or center, section 102 is substantially circular in shape. The second section (or "tail") 104 or third (tail) section 107 has the shape of a narrow, elongate rectangle that extends in a first radial direction from the periphery of the first section 102. The third section 107 is shown extending in a second radial direction from the periphery of the first section. Where the center section and the tail section join at intersection 105 (or 111) (which represent the beginning of the tail section), the periphery of the center section has a straight portion and the width of the tail section may be reduced (not shown). The fourth, or tab, section 106 has the shape of a broad, elongate rectangle that extends in a third radial direction from the periphery of the center section 102. Preferably, at least one tail section, and tab section are aligned along a diameter of the center section. In at least one embodiment, the first or second tail section and tab section are separated by an arc of less than or equal to 180° on the periphery of the center section.

The elements of the electronic circuit can be disposed on a single surface, on a first side 108 of the flexible substrate. In at least one embodiment, the third thermal sensor can be disposed on an opposite side from the second or first thermal sensors. A first thermal sensor 120 is positioned inside the outer perimeter 125 of the center section 102, preferably, near or at the center of the center section 102. An electrically conductive heater trace 122 defines a heater with a shape that surrounds, encompasses, or encircles a zone 121 in which the first thermal sensor 120 is located. In at least one embodiment, the zone 121 can be thermally isolated/insulated from the heater trace such that the thermal sensor is substantially unaffected by the heater trace 122. The heater trace 122 is shown as having an annular shape that includes a circular array of wedge-shaped heater zones 124 that surround or encircle the zone 121 and the first thermal sensor 120 which is disposed in the zone 121. A second thermal sensor 126 is positioned on the tail section 104. In at least one embodiment, the second thermal sensor 126 can have an insulation 129 disposed thereon to prevent thermal interference from the outside environment. A third thermal sensor 127 is positioned on the tail section 107.

The third thermal sensor 127 can be isolated from the heater trace (when a device is assembled). A plurality of electrical connection pads 130 is located in the tab section 106. The heater trace includes two electrically conductive trace sections that terminate in the connection pads 130 *a* and 130 *b*. For illustrative purposes, only one of the electrically conductive traces is shown. More connection pads for a sensor can be possible. An electrically conductive trace extends between mounting pads on which the first thermal sensor 120 is mounted and the connection pad 130*e*. An electrically conductive trace extends between the second thermal sensor 126 is mounted and the connection pad 130*d*.

An electrically conductive trace extends between the third thermal sensor 127 and the connection pad 130c.

In at least one embodiment, the thermal sensor 126 in the tail section 104 can be spaced-apart from a portion of the perimeter 125 of the center section (e.g., from 105) at standoff distance 123. The standoff distance 123 can be sufficient for the thermal sensor 126 to be substantially aligned (e.g., 202 discussed herein) with thermal sensor 120 when in a folded-together configuration with an insulator.

The thermal sensor 127 in the tail section 107 can be spaced-apart from a portion of the perimeter 125 of the center section (e.g., from 111) at standoff distance 131. The standoff distance 131 is sufficient to allow the thermal sensor 127 to be thermally isolated (e.g., unaffected) by the heater zones 124 (e.g., when assembled into a device). In at least one embodiment, the standoff distance 131 is greater than standoff distance 123. The standoff distance 131 can also be greater than a point to point dimension of the perimeter 125.

In addition, there may also be a standoff distance 129 between the thermal sensor 120 and the thermal sensor 126. In at least one embodiment, the standoff distance 129 is at least twice a radial dimension from the thermal sensor 120 to a point of the perimeter 125. The standoff distance 129 can also be at least twice a radial dimension from the thermal sensor 120 to a point of the perimeter 125.

In the specific layout shown in FIG. 1, the path of the heater trace 122 crosses the paths of the two traces for the second thermal sensor 126. In this case, the continuity of the heater trace is preferably, but not necessarily, maintained by an electrically conductive zero-ohm jumper 132 which crosses, and is electrically isolated from, the two traces for the thermal sensors 126 and 127. In other embodiments, the continuity of the heater trace 122 can also be maintained by vias to the second side of the flexible substrate, by running the thermal sensor traces around the periphery of the first side of the flexible substrate, by a jumper wire instead of the zero-ohm resistor, or by any equivalent solution. In at least one embodiment, the heater trace 122 is concentric with the center section 102 meaning that the heater trace 122 generally is circular.

The flexibility or conformability of the flexible substrate 100 can be enhanced by a plurality of slits 133 that define zones which move or flex independently of each other. In the preferred embodiment, the slits 133 are made in the center section 102 in a pattern that follows or accommodates the layout of the heater trace 122. The pattern at least partially separates the heater zones 124 to allow any one of the heater zones 124 to move independently of any other heater zone. The pattern of slits can be a radial pattern in that each slit is made along a respective radius of the circular center section 102, between adjacent heater zones, and extends along the radius from the periphery of the center section 102 toward the center of the circular shape of the section. In at least one embodiment, the pattern of slits 133 can define a space where the heater trace 122 occupies. The heater trace 122 can also be multi-zone meaning that the heater trace 122 is divided into separate heating zones. This is not meant to exclude other possible slit configurations determined by the different shapes of the heater trace layout and the flexible substrate sections.

In at least one embodiment, sections of the flexible substrate 100 are brought or folded together about an insulator to provide thermal resistance between the first and second thermal sensors 120 and 126 in a configuration that is preferred for ZHF temperature measurement. For example, at least the center and tail sections 102 and 104 of the flexible substrate are brought or folded together about a flexible insulator. Preferably, the first and second thermal sensors 120 and 126 are thereby disposed on respective sides of a thermal insulator. As shown in FIG. 2, the center section 102 and tail section 104 are folded together about a flexible layer of insulating material 140. The layer 140 provides thermal and electrical resistance between the thermal sensors; it also supports the thermal sensors in a spaced-apart configuration.

A flexible temperature measurement device construction includes an electrical circuit laid out on a side of a flexible substrate as shown in FIG. 1. With two sections of the flexible substrate brought or folded together to sandwich a flexible insulator, the construction has a multilayer structure as best seen in FIG. 2. Thus, a temperature measurement device 200 includes the electrical circuit laid out on the surface of the first side 108 of the flexible substrate 100. The central and tail sections 102 and 104 are brought or folded together about the flexible insulating layer 140 to provide a thermal resistance between the first and second thermal sensors 120 and 126. The flexible insulating layer also maintains the first and second thermal sensors disposed in a spaced relationship. The second thermal sensor 126 can be aligned with the first thermal sensor a line 202 which passes through the zone 121 that is surrounded by the heater trace (seen in FIG. 1). The temperature measurement device further can also include a flexible heater insulator 208 attached to a first side 109 of the substrate 100, over the center section 102. In at least one embodiment, the zone 121 is thermally isolated from the heater trace such that the heater trace does not induce heat via induction or conduction to the first thermal sensor 120.

The layout of the electrical circuit illustrated in FIG. 1 locates all of the circuit components on a single surface on one side of the flexible substrate 100. This layout confers several advantages. First, it requires only a single fabrication sequence to lay down traces for the heater, the thermal sensors, and the connection pads, thereby simplifying manufacture of the device. Second, when the sections carrying the thermal sensors are folded together, the thermal sensors are maintained within a thermally and mechanically controlled environment.

Another benefit of the layout shown in FIG. 1 is that the first thermal sensor 120 is physically removed from the heater, in a zone 121 of zero vertical heat flux that is surrounded or encircled by the heater trace 122, and not stacked under it as in the Fox/Solman and Togawa systems. When the temperature measurement device is activated, the heater is turned on and the heat produced thereby travels generally vertically from the heater to the patient, but only medially to the first thermal sensor. As a result, the jump in temperature that occurs when the heater is activated is not immediately sensed by the first thermal sensor, which improves stability of the temperature measurement without requiring an increase in thermal mass of the temperature measurement device. Thus, the first thermal sensor 120 is preferably located in the same plane, or on the same surface, as the heater trace 122 (and can even be elevated slightly above the heater trace), and substantially in or in alignment with the zone 121 of zero heat flux.

It is desirable that the temperature measurement device support a pluggable interface for convenience and for modularity of a patient vital signs monitoring system. In this regard, and with reference to FIGS. 1 and 2, the tab section 106 is configured with the array of pads 130 to be able to slide into and out of connection with a plug. In order to provide a physically robust structure capable of maintaining its shape while being connected and disconnected, the tab section 106 is optionally stiffened. In this regard, a flexible stiffener 204 is disposed on the second side 109 of the flexible substrate 100. The stiffener extends substantially coextensively with the tab section 106 and partially over the center section 102, at least to the location of the first thermal sensor 120.

As best seen in FIG. 2, the stiffener 204 is disposed between the second side 109 of the flexible substrate 100 and the flexible insulator 208. A key to align the tab section 106 with an electrical connector (not shown) and to retain the connector on the tab section may be provided on the device 200. For example, with reference to FIG. 1, such a key includes an opening 209 through the stiffener and tab section. In operation, the opening 209 would receive and retain a retractable, spring-loaded pawl on the casing of a plug.

The temperature measurement device 200 is mounted on a region of skin 201 where temperature is to be measured with the second thermal sensor 126 closest to the skin 201. A layer of adhesive 222 is disposed on the second side 109, on the layer of insulation 140 and the portion of the tail section 104 where the second sensor 126 is located. A release liner (not shown in this figure) may be peeled from the layer of adhesive 222 to prepare the device 200 for attachment to the skin. When deployed as shown in FIG. 2, a pluggable signal interface between the electrical circuit on the device 200 and a temperature control mechanization is provided through the plurality of electrical connection pads 130 located in the tab section 106. The signals transferred therethrough would include at least heater activation and thermal sensor signals.

In addition, FIG. 2 illustrates the tail section 107 being deployed on the skin 201 of a patient. The tail section 107 can extend past the center section 102 such that the tail section 107 does not overlap with any portion of the center section 102 or the tail section 104. The thermal sensor 127 can be attached to the skin 201 through an adhesive 221 such that the skin temperature of the skin 201 is received by the sensor 127. The tail section 107 can form a substantially-triangular (or wedge-shaped) gap 224 defined by the point 111 (where the tail section 107 joins with center section 102), the perimeter base 223 of the temperature device adjacent to the thermal sensor 127, and the edge of the adhesive 221.

FIG. 3 illustrates an embodiment of a temperature device (flexible) substrate 300 which is similar in construction to temperature substrate 100 of FIGS. 1 and 2 except that a tail section has at least two thermal sensors.

The temperature device substrate 300 can have a tail section 301 with two portions, 304, and 307. The tail section 301 can meet a perimeter of the center section at 305. A sensor 326 can be disposed on portion 304. The sensor 326 can be at a standoff distance 323 from 305. Another standoff distance 329 can exist between sensor 326 and sensor 320. In at least one embodiment, the term tail section can refer to a continuous element extending from the center section. A single tail section can have multiple portions which can be denoted by features. As shown in FIG. 3, the feature is the change of angle which indicates a new portion. In at least one embodiment, a feature can also be an attachment to another portion (i.e., if a first portion was detachable from the second portion).

The portion 307 can have a sensor 327. In at least one embodiment, the thermal sensor 327 can have a insulation 330 disposed on the substrate and/or proximate to the sensor to prevent thermal interference from the outside environment. The portion 307 is depicted as 90 degrees from an axis formed by the portion 304, however many angles between 0 to 180 degrees are possible. The resulting temperature device can have a skin thermal sensor that is approximately 90 degrees from the axis formed by the connector pads and the thermal sensor 320. The sensor 327 can be spaced-apart from the sensor 326. For example, sensor 327 can have a standoff distance 325 from sensor 326.

In at least one embodiment, the standoff distance 325 is greater than standoff distance 323. The standoff distance 323 is greater than a point to point dimension of a perimeter of the center section. Further, the standoff distance 329 can be at least twice radial dimension from the first thermal sensor 320 to a perimeter of the center section. Standoff distance 325 can be at least a radial dimension from the first thermal sensor 320 to a perimeter of the center section.

FIG. 4 illustrates an embodiment of a temperature device 400. The device 400 is similar in construction to temperature device 200 in FIG. 2 except that the tail portion 307 is attached to or formed integrally with the tail portion 304. The device 400 includes an insulation layer 307. The flexible substrate 300 has a first side 308 and a second side 309.

In at least one embodiment, the thermal sensor 326 and thermal sensor 327 can be disposed on opposite sides of the flexible substrate 300. For example, the sensor 327 can be disposed on the second side 309 (e.g., outside surface). The sensor 326 and 320 can be disposed on the first side 308 (e.g., inside surface).

Insulation 340 can contact the first side 308 while another insulation 408 can be disposed proximate to the second side 309. Adhesive layers 422 and 421 can be disposed on the second side 309. The adhesive layers 422 and 421 can be any skin-compatible adhesive and with sufficient adhesion to allow the temperature device 400 to adhere to skin. In at least one embodiment, the tail portion 307 can extend past the axis 404 which is based on an alignment of the insulation layers and/or a portion of the substrate 300. The tail portion 307 can be formed from the same substrate as the portion holding the sensor 326. In at least one embodiment, the thermal sensor 327 can be on the same plane as sensor 326. An advantage of this set up is that the substrate remains close to the skin of the patient and is less likely to snag.

Use of an electrical circuit on a flexible substrate greatly simplifies the construction of a disposable temperature device for estimating deep tissue temperature, and substantially reduces the time and cost of manufacturing such a device. In this regard, manufacture of a temperature measurement device incorporating an electrical circuit laid out on a side of the flexible substrate 100 with the circuit elements illustrated in FIG. 1 may be understood with reference to FIGS. 5 and 6A-6F. Although a manufacturing method is described in terms of specifically numbered steps, it is possible to vary the sequence of the steps while achieving the same result. For various reasons, some of the steps may include more operations, or fewer, than described. For the same or additional reasons, some of the described steps may be deleted, and/or other steps that are not described may be added. Further, steps may be combined with other steps, and/or partitioned into additional steps.

Figure 6A:
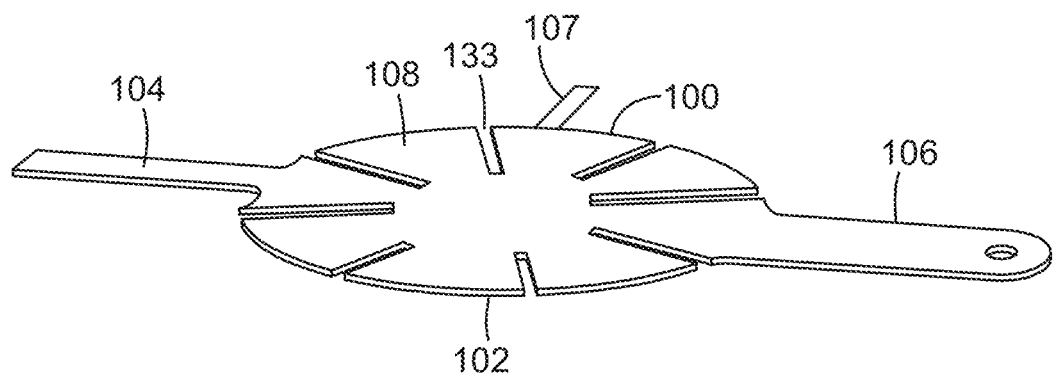
FIGS. 6A-6F illustrate a method of temperature device manufacture based on the temperature device of FIGS. 1 and 2, according to aspects of the present disclosure.

In FIG. 6A, the traces and pads for an electrical circuit are fabricated on a first side 108 of a flexible substrate 100 with a center section 102, a tail sections 104, 107 extending from the center section, and a tab section 106 extending from the center section. The electronic elements (first and second thermal sensors) are mounted to the traces to complete an electrical circuit (which is omitted from these figures for convenience) including the elements of FIG. 3, laid out as shown in that figure. If used, the pattern of slits 133 separating the heater zones may be made in the center section in this manufacturing step.

Figure 5:
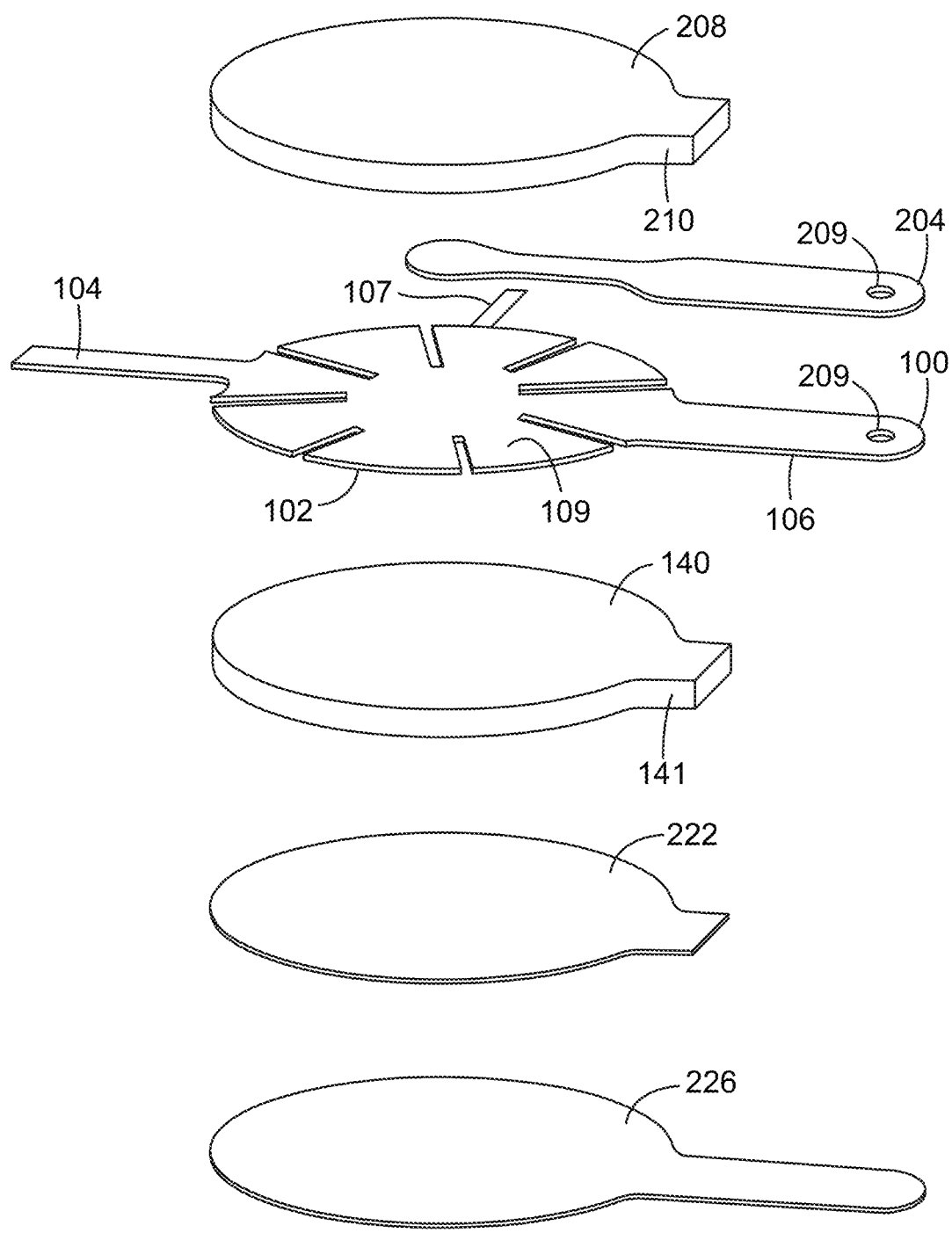
FIG. 5 is an exploded assembly view, in perspective, showing elements of the temperature device of FIG. 2, according to aspects of the present disclosure.
Figure 6B:
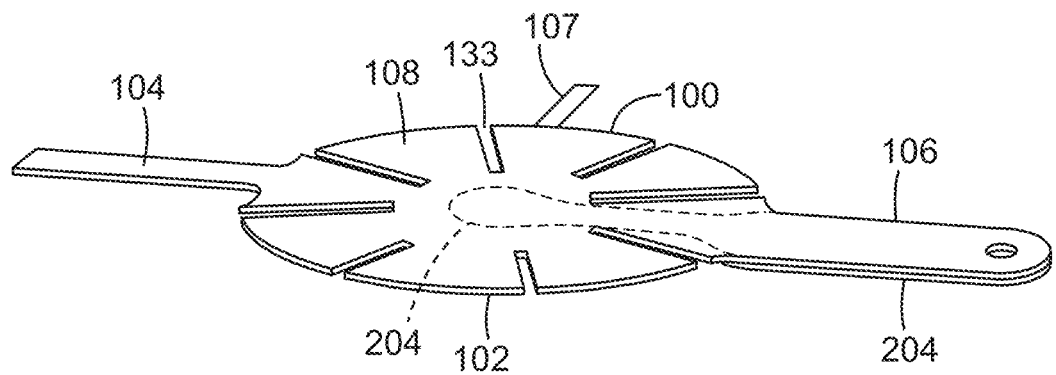
Figure 6C:
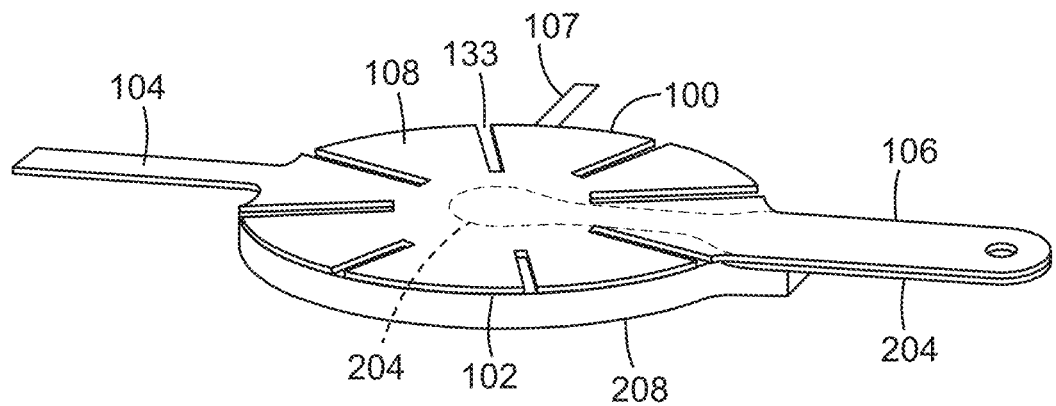

As per FIG. 6B, in a second manufacturing step, a stiffener 204 is laminated to a second side of the flexible substrate. As best seen in FIG. 5, the stiffener has a portion shaped identically to the tab section and narrows to an elongated portion with a circular tip. When laminated to the second side 109, the stiffener substantially extends over the tab section and partially over the center section, beneath the zone 121 where the first thermal sensor is located. Preferably, an adhesive film (not seen) attaches the stiffener to the second side of the flexible substrate, As per FIG. 6C, in a third manufacturing step, a flexible layer 208 of insulating material is attached by adhesive or equivalent to the first side of the flexible substrate, over substantially all of the center section and at least a portion of the stiffener. This layer is provided to insulate the heater from the ambient environment. As best seen in FIG. 5, this flexible layer may include a truncated tab section 210 that provides additional reinforcement to a pluggable connection between the tab section 106 and a system plug.

Figure 6D:
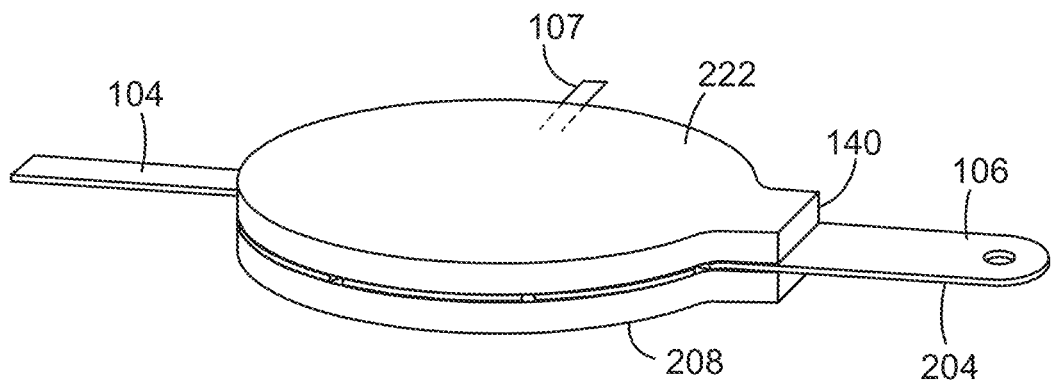

As per FIG. 6D, in a fourth manufacturing step, a flexible central layer of insulating material 140 is attached to the first side 108, over the center section, to cover the heater trace and the first thermal sensor. As best seen in FIG. 5, this flexible layer may also include a truncated tab section 141 that provides additional reinforcement to a pluggable connection between the tab section and a system plug.

Figure 6E:
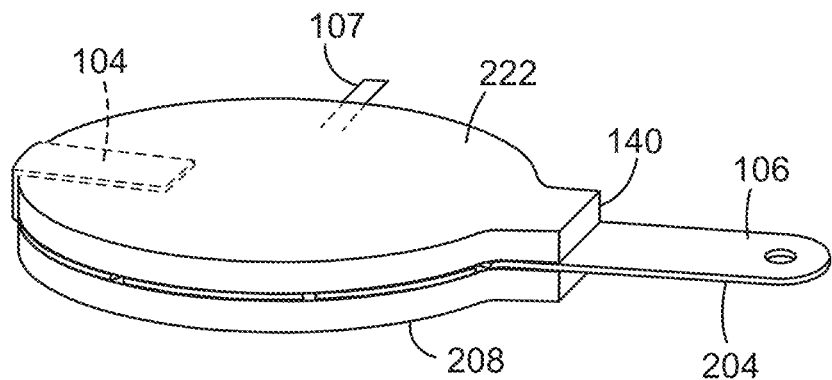

As per FIG. 6E, in a fifth manufacturing step, the tail section 104 is folded over the central layer of insulating material 140 such that the first and second thermal sensors are maintained by the central layer in the preferred spaced relationship. The tail section 107 is left free and unattached. In at least one embodiment, a portion of the surface of insulation layer 108 may have a release liner such that the adhesive section of 107 can be releasably attached to the portion of 222.

Figure 6F:
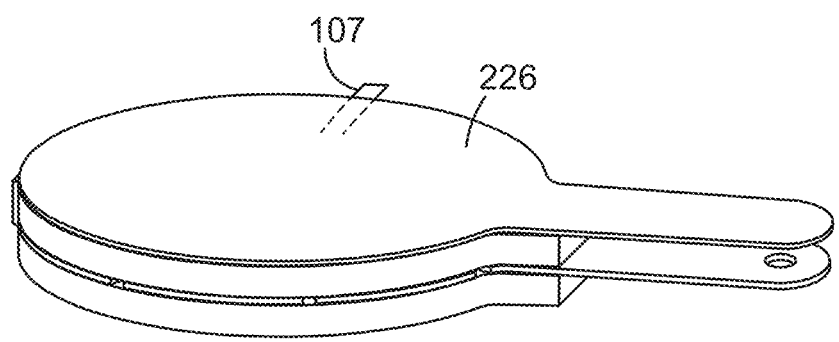

As per FIG. 6F, in a sixth manufacturing step, a layer of adhesive with a release liner 226 is attached to the central insulating layer, over the central insulating layer with the tail section folded thereto. As best seen in FIG. 5, the release liner 226 may have a shape that corresponds to the center section 102 and tab section 106.

Figure 7:
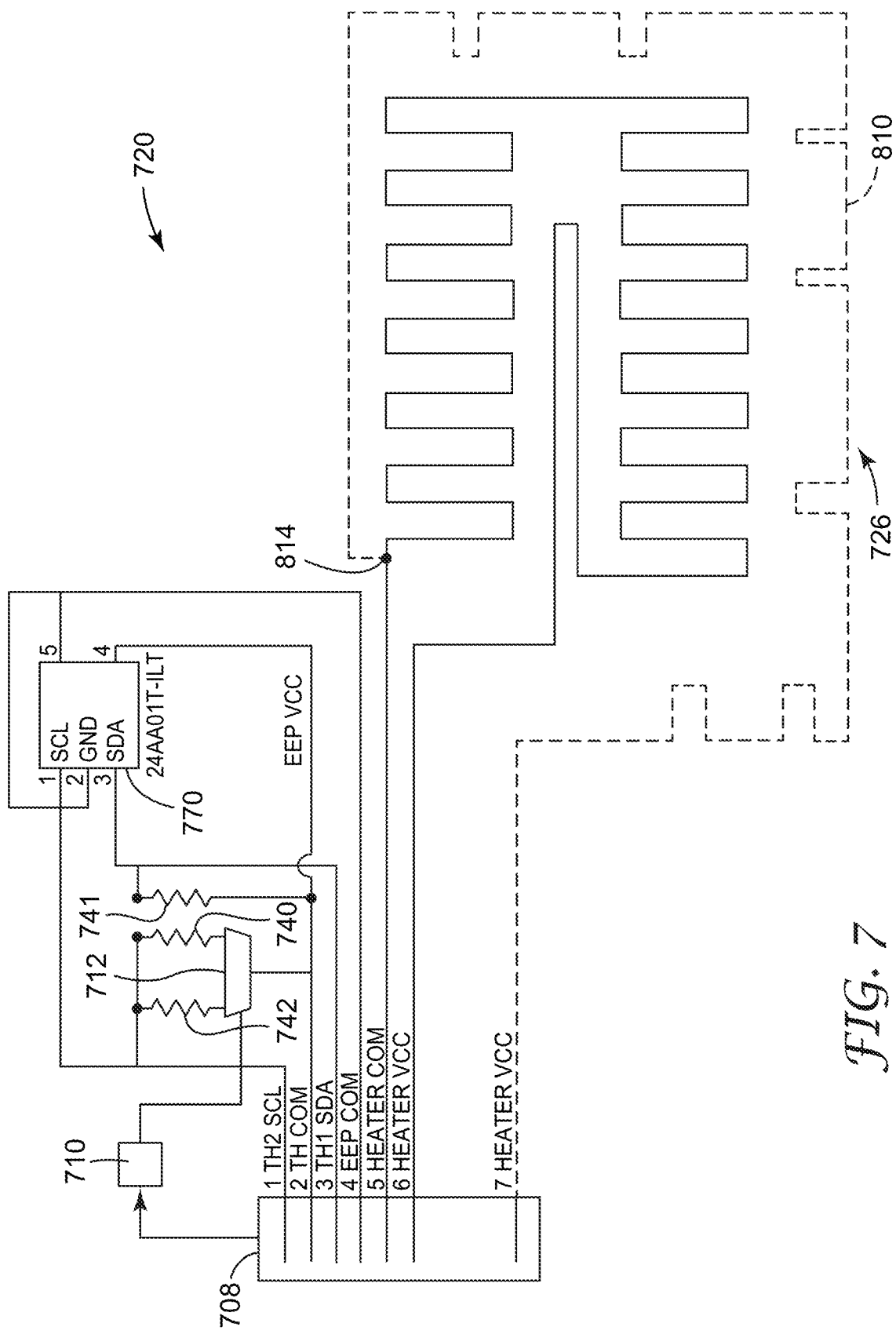
FIG. 7 is a schematic diagram including elements of the temperature device, according to aspects of the present disclosure.

The layout of FIG. 1 and the corresponding electrical circuit of FIG. 7 illustrate an interface by which operation of a zero-heat-flux deep tissue (DTT) measurement device can be controlled and monitored in a DTT control mechanization. Electrical circuit 720 is disposed on a flexible substrate. The electrical circuit 720 includes at least an electrically conductive heater trace, thermal sensors, electrically conductive connective trace portions, and electrical connection pads. The electrical circuit includes a heater 726, a first thermal sensor 741, and a second thermal sensor 740, and a third thermal sensor 742. The third and second thermal sensors 740, 742 can be coupled to a switching device (e.g., a multiplexer) 712. The switching device 712 can be controlled based on signals received from one or more connection pads of the tab section 708.

It is desirable that some, but not necessarily all, embodiments of the electrical circuit 720 also include at least one multi-pin electronic circuit device, such as an electronically programmable memory 770. The heater trace 724 defines a generally annular heater 726 surrounding a zone 730 of the substrate 701 into which no portion of the heater trace 724 extends; in this regard, the zone 730 is not directly heated when the heater operates. In at least one embodiment, the heater trace 726 can be divided into independently controlled traces. For example, the heater trace 726 includes three traces: a first trace 810 that defines the central heater portion, a second trace surrounding the first trace 810, that defines the peripheral heater portion, and a third trace connected to the first and second traces at a shared node 814.

Figure 8:
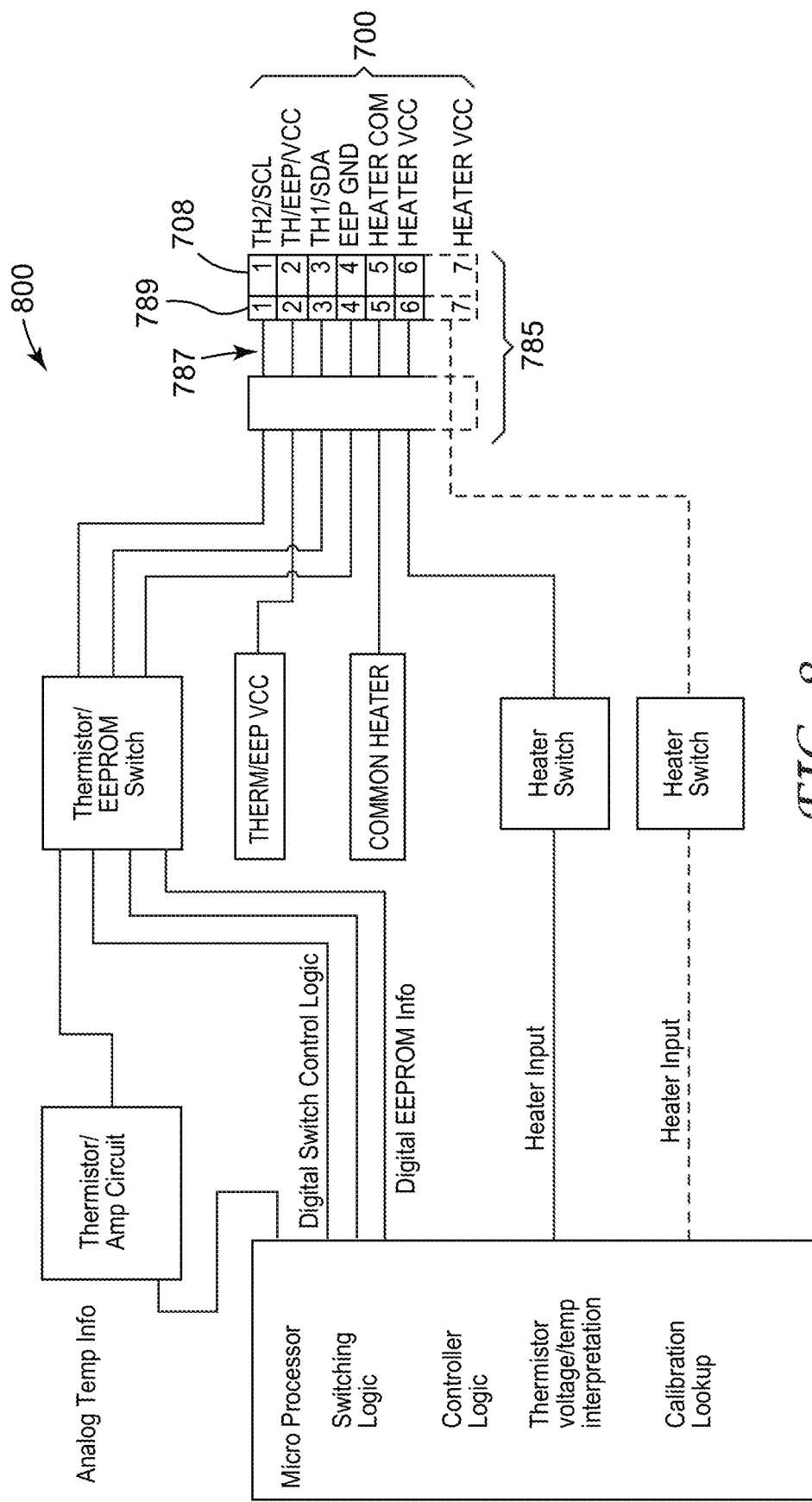
FIG. 8 is a block diagram illustrating a temperature control mechanization, according to aspects of the present disclosure.

FIG. 8 illustrates a signal interface between a zero-heat-flux DTT measurement device according to FIG. 7. With reference to these figures, a DTT control mechanization includes control mechanization 800, a measurement device 700, and an interface 785 that transfers power, common, and data signals between the control mechanization and the measurement device. The interface can be wireless, with transceivers located to send and receive signals. Preferably, the interface includes a cable 787 with a connector 789 releasably connected to the tab section 708. The control mechanization 800 manages the provision of power and common signals on respective signal paths to the heater and provides for the separation of the signals that share a common signal path, such as the Thermistor2 (TH2) and SCL signals. A common reference voltage signal is provided on a single signal path to the thermal sensors, and respective separate return signal paths provide sensor data from the thermal sensors.

Presuming inclusion of an EEPROM on the measurement device 700, a separate signal path is provided for EEPROM ground, and the thermal sensor signal paths are shared with various pins of the EEPROM as per FIG. 8. This signal path configuration separates the digital ground for the EEPROM from the DC ground (common) for the heater, for good reason. Presume that the EEPROM and the heater share an electrical pad for ground. The cable 787 including its connector contacts has a certain amount of resistance. If the heater 726 is powered up, the current through it has to return to the control mechanization 800 through the ground (common) contact, which means there will be some voltage developed on the measurement device side of the contact equal to the resistance of that line multiplied by the current through the heater 726. That voltage could be as high as 2 or 3 volts depending on the integrity of the contacts. If concurrently the supply voltage goes low on the EEPROM or even one of the logic lines goes low below this aforementioned generated voltage, the EEPROM would be reversed biased which could damage the part. Separating the heater and EEPROM grounds eliminates all these possibilities for damage to the EEPROM. Accordingly, it is desirable to electrically isolate the heater altogether from the other elements of the electrical circuit. Thus, as per FIG. 8, a first electrical pad (electrical pad 5, for example) of the plurality of electrical pads is connected only to a first terminal end of the heater trace, while a second electrical pad (electrical pad 6, for example) of the plurality of electrical pads is connected only to the second terminal end of the heater trace.

With reference to FIG. 7, presume that the thermal sensors are NTC (negative temperature coefficient) thermistors. In this case, the common signal on electrical pad 2 is held at a constant voltage level to provide Vcc for the EEPROM and a reference voltage for the thermistors. Control is switched via the thermistor/EEPROM switch circuit between reading the thermistors and clocking/reading/writing the EEPROM.

Figure 9:
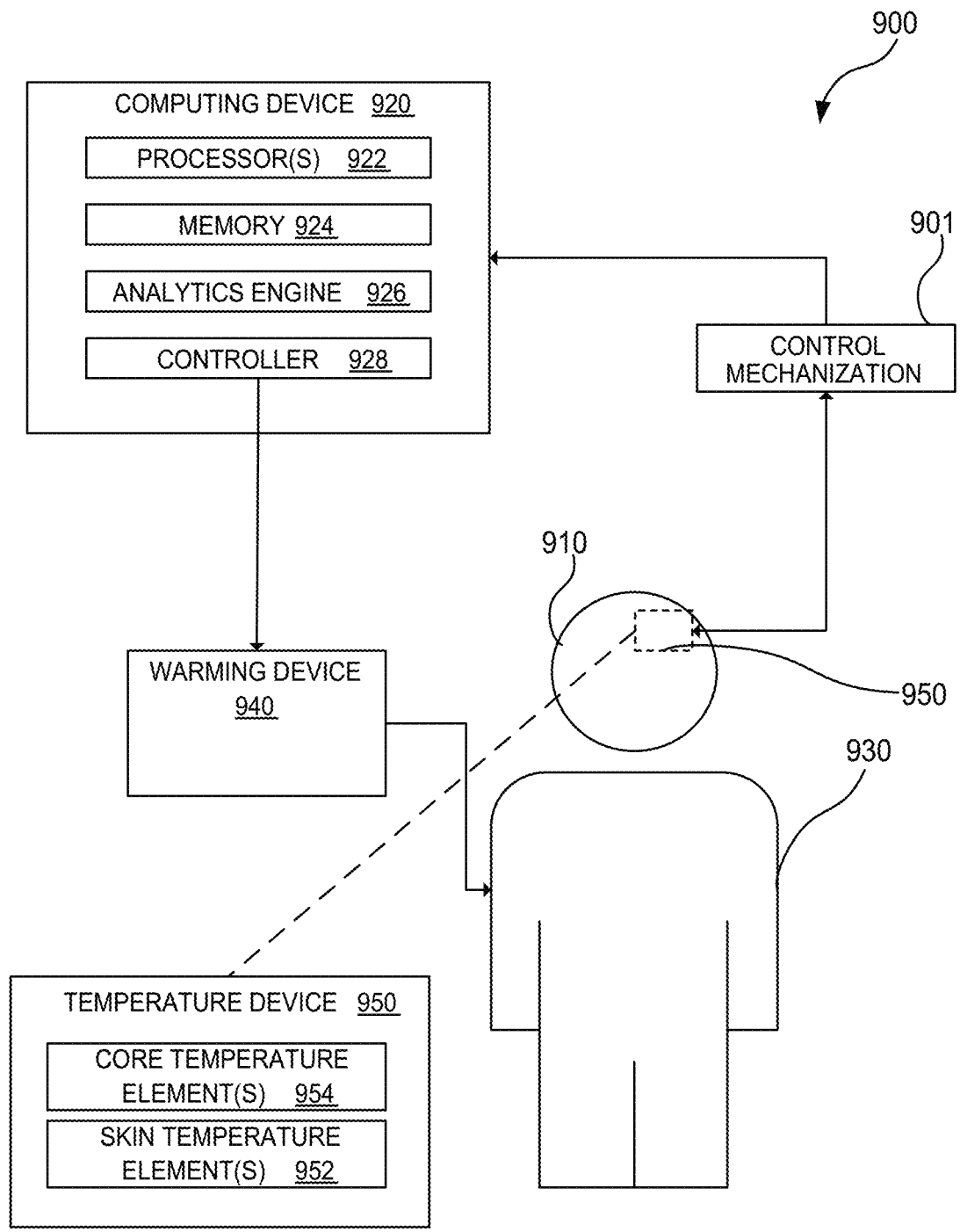
FIG. 9 is a block diagram illustrating a temperature management system, according to aspects of the present disclosure.

FIG. 9 discloses a temperature management system 900 for monitoring a core temperature and skin temperature of a patient and controlling a warming unit based on the core temperature and skin temperature of the patient.

The system 900 can have a temperature device 950 and a control mechanization 901. The temperature device 950 can have a core temperature element 954 and a skin temperature element 952. The temperature device 950 can be unheated or a zero-heat flux temperature device as described herein. For example, the temperature device 950 can be the temperature device of any of FIGS. 1-7 described herein. The temperature device 950 can be attached or coupled to a patient 930 in any position. In at least one embodiment, the temperature device 950 can be attached to the head 910 of the patient proximate to a temporal artery or carotid artery.

As mentioned herein, a skin temperature element 952 of the temperature device 950 can be used to measure a skin temperature of the patient (e.g., on the periphery of the patient). The skin temperature element 952 can be a thermal sensor that is unaffected or minimally affected by the core temperature element 954.

The temperature device 950 can be communicatively coupled to the control mechanization 901. The control mechanization 901 can process signals (e.g., electrical if wired or radio signals if wireless) from the temperature device 950 and determine both a core temperature and a skin temperature for the patient 930. The control mechanization 901 can also provide control to the various sensors in the temperature device 950. For example, the control mechanization 901 can activate the heating function of the core temperature elements 954. In at least one embodiment, the control mechanization can be arranged like control mechanization 800 in FIG. 8.

The control mechanization 901 can communicate with a computing device 920. The computing device 920 can receive the core temperature and the skin temperature of the patient 930 from the control mechanization 901 and determine one or more settings of a warming device 940. The computing device 920 can have one or more processors 922 configured to execute instructions. The computing device 920 can have a memory 924 where instructions are stored.

The computing device 920 can also have an analytics engine 926 and a controller 928. Although shown as a separate component, the computing device 920 can be a part of either the control mechanization 901, the warming device 940, or combinations thereof. The analytics engine 926 can analyze the core temperature and the skin temperature from the patient 930 at various intervals. The analytics engine 926 can perform the operations described herein. The controller 928 can analyze the control settings (e.g., temperature, fan speed, cycle time, or combinations thereof) of the warming device 940 and determine updated control settings for the warming device 940 based on the analytics engine 926.

Figure 10:
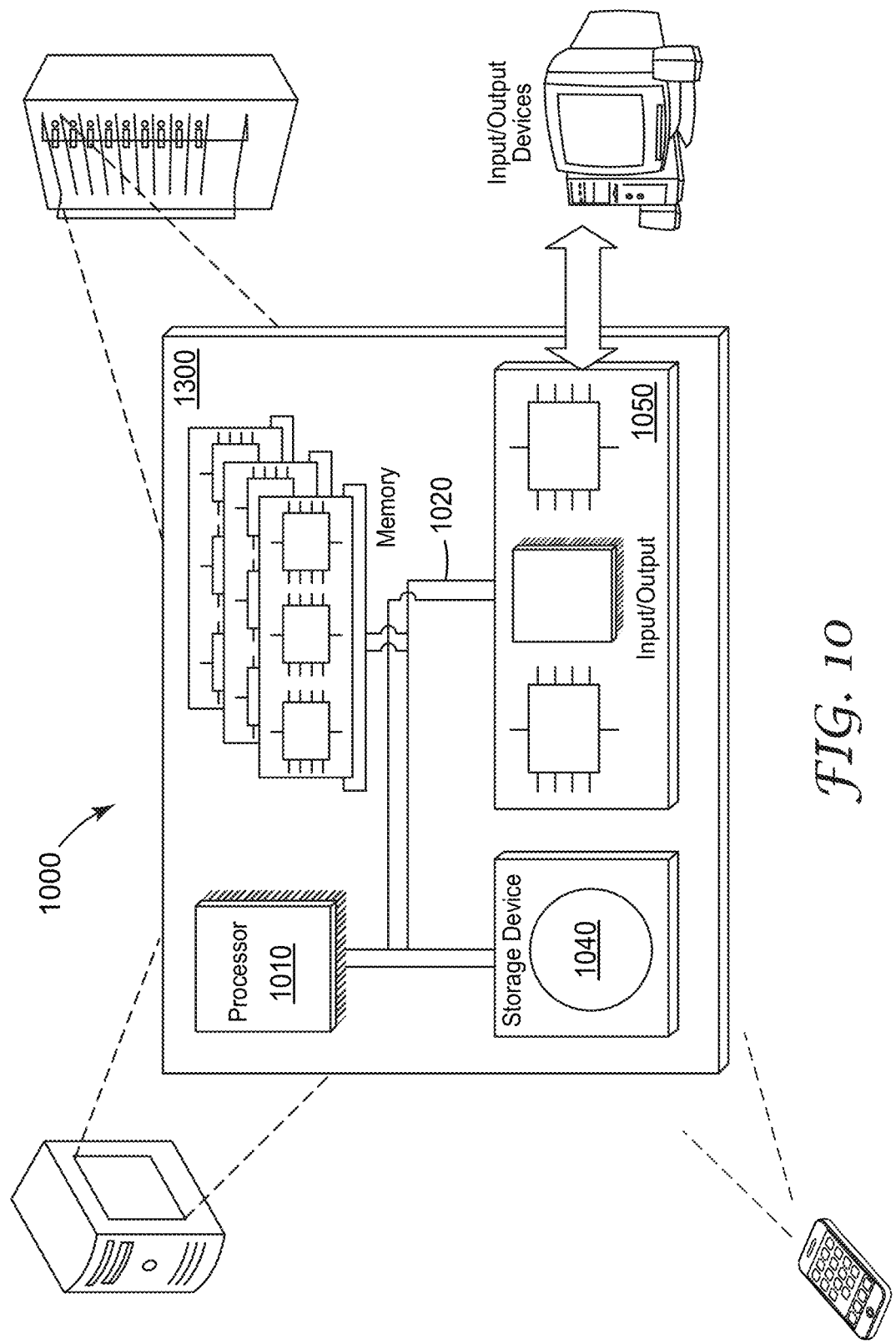
FIG. 10 is a block diagram illustrating a computing device, according to aspects of the present disclosure.

FIG. 10 shows a detailed example of various devices that may be configured to execute program code to practice some examples in accordance with the current disclosure. For example, computing device 1000 may be a computing device that performs any of the techniques described herein. In the example illustrated in FIG. 11, a computing device 1000 includes a processor 1010 that is operable to execute program instructions or software, causing the computer to perform various methods or tasks. Processor 1010 is coupled via bus 1020 to a memory 1030, which is used to store information such as program instructions and other data while the computer is in operation. A storage device 1040, such as a hard disk drive, nonvolatile memory, or other non-transient storage device stores information such as program instructions, data files of the multidimensional data and the reduced data set, and other information. The computer also includes various input-output elements 1050, including parallel or serial ports, USB, Firewire or IEEE 1394, Ethernet, and other such ports to connect the computer to external device such as a printer, video camera, surveillance equipment or the like. Other input-output elements may include wireless communication interfaces such as Bluetooth, Wi-Fi, and cellular data networks.

Figure 11:
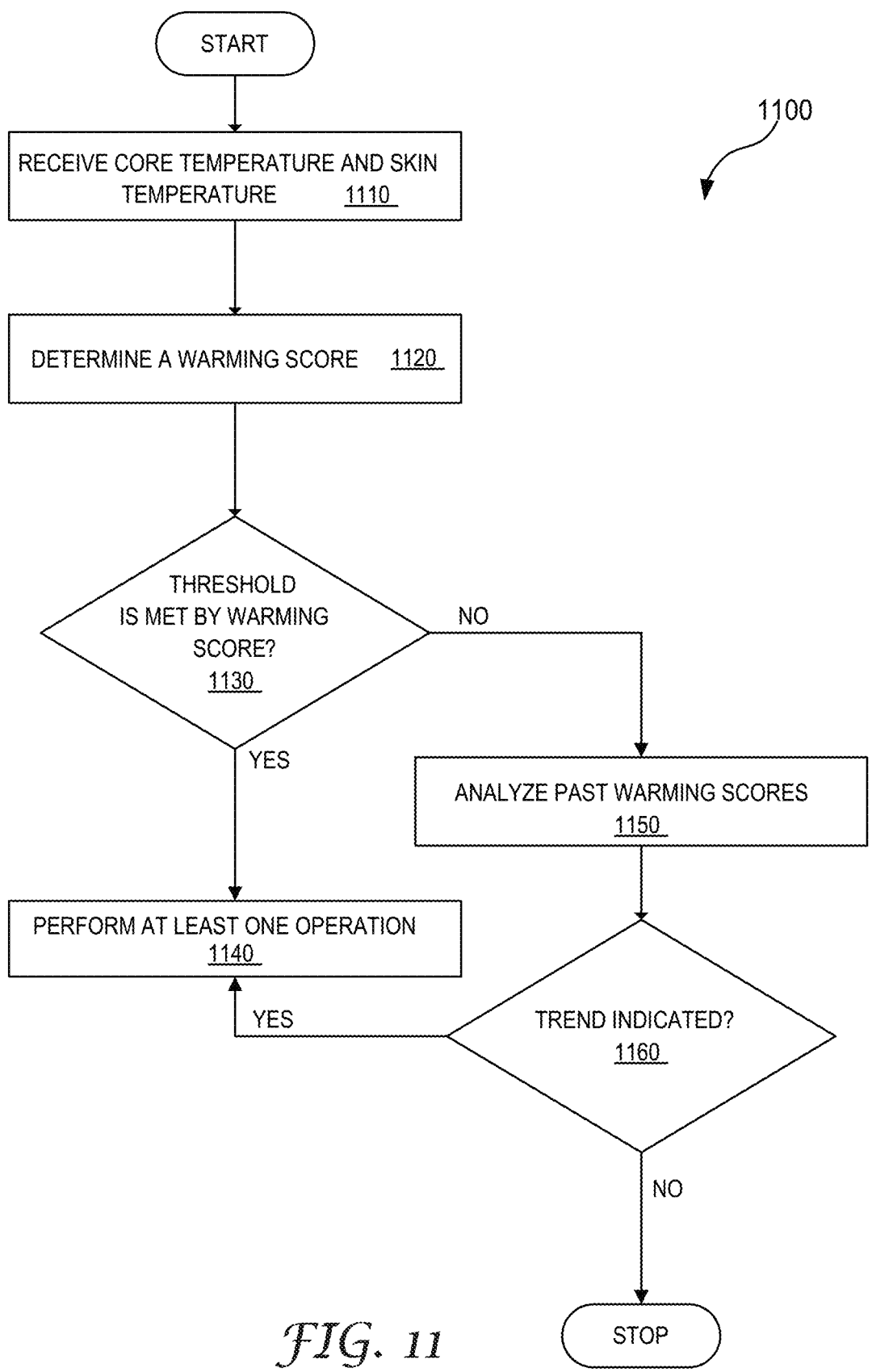
FIG. 11 is a flowchart of a method for managing temperature of a patient, according to aspects of the present disclosure.

FIG. 11 illustrates a flowchart of a method 1100 for analyzing the skin temperature and core temperature of a patient. The method 1100 can begin at block 1110.

In block 1110, the computing device can receive the core temperature and the skin temperature from the control mechanization. As discussed herein, the temperature device can have sensors to measure both the skin temperature and the core temperature of a patient. The signals from the sensors can be received by the control mechanization (e.g., electrically or via radio frequency) and processed.

In block 1120 the computing device can determine a warming score. The warming score can be indicative of the adequacy of warming for the patient. Warming can be accomplished by applying convective, conductive, or infrared energy to the patient. As the patient absorbs energy, the body temperature of the patient may increase. If the core temperature of the patient increases past a threshold, vasodilation or even sweating may occur which can rapidly cool the patient and potentially negate any warming benefits. In at least one embodiment, the warming score can indicate the likelihood of the patient to undergo vasodilation Although various metrics can be used, the warming score can be based on the relationship between the core temperature and the skin temperature. In at least one embodiment, the warning score can be based on a difference between the core temperature and the skin temperature of the patient.

Figure 12:
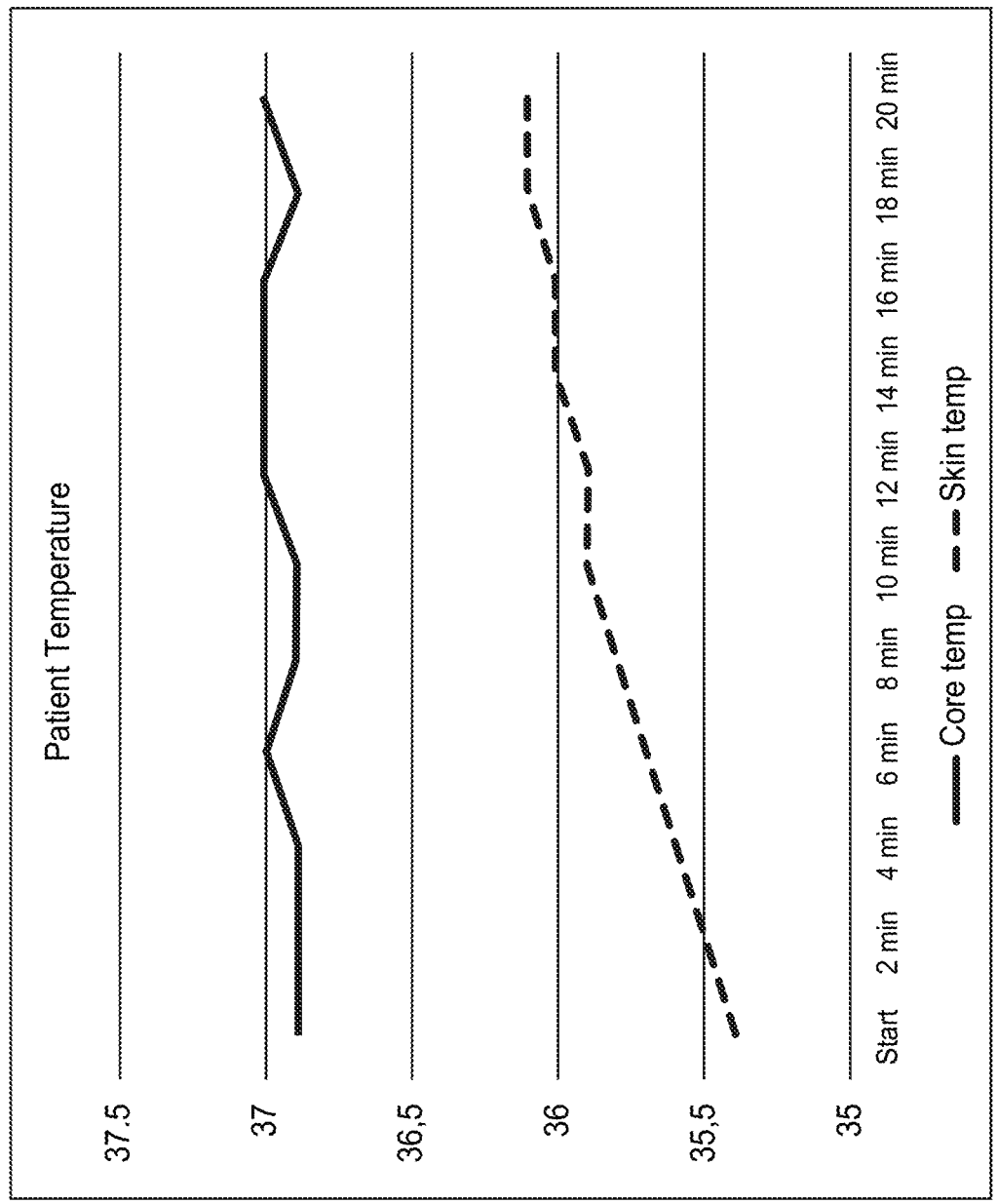
FIG. 12 is an exemplary chart of patient core temperature and skin temperature over time, according to aspects of the present disclosure.

An exemplary graph is provided in FIG. 12 charting both the skin temperature of the patient and the core temperature. The core temperature is maintained at approximately 37 degrees Celsius while the skin temperature is rising (therefore decreasing the difference). The warming score can be based on this difference in temperatures. In at least one embodiment, pre-warming can also be measured (which is warming the patient prior to surgery).

In block 1130, the computing device can determine whether a warning score meets a threshold. The threshold can be based on adequate warming or inadequate warming. If the threshold is based on a difference between core temperature and skin temperature, a difference of no greater than +0.1, 0.2, 0.3, 0.4, 0.5, 0.6, 0.7, 0.8, 0.9, 1, or 2, degrees Celsius can indicate adequate warming (meaning that the threshold is met). In at least one embodiment, if the skin temperature of the patient is above the core temperature, then it may be indicative of adequate pre-warming of the patient.

In block 1140, the computing device can perform at least one operation based on the warming score meeting the threshold. For example, the operation can include interacting with the controller to change the first heat setting to the second heat setting. The heat setting can include a temperature level, a fan speed, or combinations thereof. In at least one embodiment, the first heat setting can be higher than the second heat setting. For example, in response to a warming score indicating that the patient is warmed, the computing device can instruct the warming device to reduce the energy transfer to the patient. Alternatively, the computing device can also instruct the warning device to increase energy transfer to the patient.

In at least one embodiment, the operation can also be changing any display settings of the computing device. For example, a color of a font for the temperature. The operation can also trigger an a prediction of total time left in a pre-warning cycle of the warming device. For example, the prediction can be based on a rate of change between the core and skin temperatures and the beat applied by the warming device.

In block 1150, the computing device can analyze prior warning scores determine whether prior warming scores indicate trend of increasing or decreasing values. In at least one embodiment, the trend is a rising difference between consecutive scores determined in block 1120. For example, in FIG. 12, the temperature difference appears to be decreasing over successive readings of temperature differences of the patient. In at least one embodiment, the trend can be based on point-to-point values of successive readings. Various statistical techniques can be used to account for spikes of scores off-trend such as rolling averages, or area under the curve. For example, if the overall trend is increasing but a point-to-point value shows decreasing, then rolling averages can remove the trend.

In block 1160, the computing device can determine if a trend is indicated and, if so, perform at least one operation based on the trend in block 1140.

Various examples and implementations will be described in detail. These examples should not be construed as limiting the scope of the present disclosure in any manner, and changes and modifications may be made without departing from the spirit and scope of the disclosure. Further, only some end uses have been discussed herein, but end uses not specifically described herein are included within the scope of the present disclosure. As such, the scope of the present disclosure should be determined only by the claims.

LIST OF ILLUSTRATIVE EMBODIMENTS

1. A temperature device, comprising:
   a flexible substrate; and,
   an electrical circuit on a surface of the flexible substrate, the electrical circuit comprising:
   at least three thermal sensors including at least one skin thermal sensor;
   a plurality of electrical pads; and
   a plurality of conductive traces connecting at least three thermal sensors with the plurality of electrical pads.
2. The temperature device of embodiment 1, wherein two thermal sensors are arranged to measure a deep tissue temperature of a patient and a third sensor is dedicated to measure a skin temperature of the patient.
3. The temperature device of embodiment 1, wherein the electrical circuit further comprises:
   a heater trace surrounding a zone of the surface,
   a first thermal sensor disposed in the zone,
   at least two thermal sensors including a second thermal sensor and a third thermal sensor disposed outside of the heater trace,
   a plurality of electrical pads disposed outside of the heater trace, and
   a plurality of conductive traces connecting the first, second and third thermal sensors and the heater trace with the plurality of electrical pads.
4. The temperature device of embodiment 3, wherein a second thermal sensor and a third thermal sensor is disposed outside of the heater trace.
5. The temperature device of embodiment 4, in which sections of the flexible substrate are folded together to place the first and second thermal sensors in proximity to one another, between the sections.
6. The temperature device of embodiment 5, wherein the third thermal sensor is not proximate to the second thermal sensor.
7. The temperature device of any of embodiments 4 to 6, wherein a conductive trace of the second thermal sensor is proximate to a portion of a conductive trace of the third thermal sensor.
8. The temperature device of embodiment 7, wherein the conductive trace of the third thermal sensor is parallel to a portion of the conductive trace of the third thermal sensor.
9. The temperature device of any of embodiments 1 to 8, wherein the flexible substrate comprises a center section, a tab section that is contiguous with the center section and extending from the center section in a first radial direction, and a first tail section contiguous with the center section and extending from the center section in a second radial direction.
10. The temperature device of embodiment 9, wherein the flexible substrate comprises a second tail section that is contiguous with the center section and extending from the center section in a third radial direction.
11. The temperature device of embodiment 9, wherein the first tail section comprises a first tail portion extending from the center section in the second radial direction and a second tail portion and extending from the center section in a third radial direction.
12. The temperature device of embodiment 11, wherein the second tail portion is not contiguous with the center section.
13. The temperature device of any of embodiments 9 to 12, wherein the first tail section has at least two thermal sensors.
14. The temperature device of embodiment 13, wherein the second thermal sensor is disposed in the first tail portion and a third thermal sensor is disposed in the second tail portion.
15. The temperature device of embodiment 10, wherein a second thermal sensor is disposed in the first tail section and a third thermal sensor is disposed in the second tail section.
16. The temperature device of any of embodiments 9 to 15, wherein the third radial direction is the same as the second radial direction.
17. The temperature device of any of embodiments 1 to 16, wherein the first thermal sensor is disposed on the same side as the second thermal sensor.
18. The temperature device of any of embodiments 1 to 17, wherein the second thermal sensor is disposed on an opposite side as the third thermal sensor.
19. The temperature device of any of embodiments 1 to 16, wherein the zone is encompassed by the heater trace.
20. The temperature device of any of embodiments 1 to 19, wherein the zone is an area thermally insulated from the heater trace.
21. The temperature device of embodiment 19, wherein the zone is thermally isolated from the heater trace such that the heater trace does not induce heat via induction or conduction to the first thermal sensor.
22. The temperature device of any of embodiments 1 to 21, wherein the second thermal sensor is a first standoff distance from the center section.
23. The temperature device of any of embodiments 1 to 22, wherein the third thermal sensor is a second standoff distance from the center section.
24. The temperature device of embodiment 23, wherein the second standoff distance allows the third thermal sensor to be unheated by the heater trace.

25. The temperature device of embodiment 23, wherein the first or second standoff distance is measured from a perimeter of the center section.
26. The temperature device of any of embodiments 22 to 25, wherein the first or second standoff distance is measured from an intersection between the perimeter of the center section and the beginning of the second tail section.
27. The temperature device of any of embodiments 22 to 26, wherein the second standoff distance is measured from the second thermal sensor.
28. The temperature device of embodiment 27, wherein the second standoff distance is greater than the first standoff distance.
29. The temperature device of embodiment 27, wherein the second standoff distance is greater than a point to point dimension of a perimeter of the center section.
30. The temperature device of any of embodiments 1 to 29, wherein a third standoff distance between the first thermal sensor and the second thermal sensor is at least twice a radial dimension from the first thermal sensor to a perimeter of the center section.
31. The temperature device of any of embodiments 1 to 29, wherein a third standoff distance between the first thermal sensor and the second thermal sensor is at least twice a radial dimension from the first thermal sensor to a perimeter of the center section.
32. The temperature device of any of embodiments 1 to 31, further comprising a layer of flexible insulation disposed between folded-together sections and separating the first and second thermal sensors.
33. The temperature device of embodiment 32, wherein the first and second thermal sensors are positioned in a spaced-apart relationship.
34. The temperature device of any of embodiments 1 to 33, wherein the first and second thermal sensors and the heater trace are disposed on a first side of the flexible substrate, the temperature device further comprising a second flexible insulator disposed on a second side of the flexible substrate, over the center section.
35. The temperature device of any of embodiments 1 to 34, further comprising a third flexible insulator disposed on the first or the second side of the flexible substrate, over the third thermal sensor.
36. The temperature device of embodiment 34 or 35, further comprising a flexible stiffener disposed on the second side of the flexible substrate, substantially coextensively with a tab section.
37. The temperature device of embodiment 36, further comprising an electrical connector alignment key on the tab section.
38. The temperature device of any of embodiments 1 to 37, further comprising a pattern of slits formed in the center section from the substrate therein.
39. The temperature device of embodiment 38, wherein the pattern of slits defines a plurality of heater zones occupied by the heater trace.
40. The temperature device of embodiment 39, wherein the heater zones are wedge-shaped.
41. The temperature device of embodiment 39, wherein each heater zone is flexible independently of any other heater zone.
42. The temperature device of embodiment 41, further comprising a reduced width of the tail section where the center and tail sections are joined.
43. The temperature device of any of embodiments 38 to 42, wherein the pattern of slits and the heater trace define a multi-zone heater.
44. The temperature device of any of embodiments 1 to 43, wherein the heater trace has an annular shape and the center section has an annular shape, the heater trace is concentric with the center section.
45. The temperature device of any of embodiments 1 to 44, in which the heater trace includes three terminal ends and a first electrical pad of the plurality of electrical pads is connected only to a first terminal end of the heater trace, a second electrical pad of the plurality of electrical pads is connected only to a second terminal end of the heater trace, and a third electrical pad of the plurality of electrical pads is connected only to a third terminal end of the heater trace.
46. The temperature device of embodiment 44, in which the center section has a substantially circular shape and the first tail section and tab section are separated by an arc of less than or equal to 1800 on the periphery of the center section.
47. A method of temperature device manufacture, comprising:
fabricating an electrical circuit on a first side of a flexible substrate with a center section, a tab section extending from the center section, and a tail section extending from the center section, the electrical circuit including a first thermal sensor disposed on the first side, in the center section, a heater trace disposed on the first side, in the center section, around the first thermal sensor, and a second thermal sensor disposed on the first side in a tail section, wherein the electrical circuit also comprises a third thermal sensor disposed on the tail section on the first side or the second side, the electrical circuit comprises a plurality of electrical pads disposed on the first side, in the tab section, and a plurality of traces disposed on the first side and connecting the first, second, and third thermal sensors and the heater trace with the plurality of electrical pads; and then, attaching a flexible heater insulating layer to the second side, over the center section; attaching a flexible central insulating layer to the first side, over the center section; folding the tail section over the central insulating layer; and, attaching a layer of adhesive with a release liner to the central insulating layer, over the central insulating layer and the tail section.
48. The method of embodiment 47, further comprising:
forming the heater trace in a plurality of heater zones; and
forming a pattern of slits in the center section, each slit separating one heater zone from an adjacent heater zone.
49. The method of embodiment 47, further comprising, attaching a flexible stiffening layer to the second side, coextensively with the tab section and a portion of the center section, followed by attaching the flexible heater insulating layer to the second side, over the center section and a portion of the stiffening layer.
50. A system for temperature monitoring comprising:
a temperature device comprising at least a core temperature element and a skin temperature element;
a control mechanization communicatively coupled to the temperature device.
51. The system of embodiment 50, wherein the temperature device is an unheated temperature device.
52. The system of embodiment 50, wherein the temperature device is a zero-heat flux temperature device.

53. The system of embodiment 52, wherein the zero-heat flux temperature device is the temperature device of embodiments 1 to 46.

54. The system of embodiment 50, wherein the control mechanization is capable of determining a core temperature and a skin temperature for a patient based on electrically-responsive signals from the temperature device.

55. The system of embodiment 54, further comprising the patient, wherein the temperature device adheres to skin of the patient.

56. The system of any of embodiments 50 to 55, wherein the skin temperature element is positioned on a patient such that a peripheral temperature of the patient is measured.

57. The system of any of embodiments 50 to 55, further comprising:
a computing device communicatively coupled to the warming device and the control mechanization, the computing device comprising one or more computer processors and a memory comprising instructions that when executed by the one or more computer processors cause the one or more computer processors to:
receive the core temperature and the skin temperature from the control mechanization;
determine a warming score based on the relationship between the core temperature and the skin temperature;
determine whether a warming score meets a threshold;
perform at least one operation based on the warming score meeting the threshold.

58. The system of embodiment 57, further comprising a warming device having a first heat setting and a second heat setting;
wherein, to perform at least one operation, the memory comprises instructions that when executed by the one or more computer processors cause the one or more computer processors to provide instructions to the warming device to change the first heat setting to the second heat setting.

59. The system of embodiment 57 or 58, wherein the memory comprises instructions that when executed by the one or more computer processors cause the one or more computer processors to provide instructions to the warming device to:
analyze prior warming scores responsive to the threshold not being met; determine whether prior warming scores indicate a trend, and
perform at least one operation based on the trend.

60. The system of embodiment 59, wherein the warming score is indicated by a difference between a core temperature and a skin temperature.

61. The system of embodiment 60, wherein the trend is based on increasing scores between readings of the core temperature element and the skin temperature element.

62. The system of embodiment 61, wherein the trend is based on increasing scores between consecutive readings of the core temperature element and the skin temperature element.

63. The system of embodiment 61 or 62, wherein the trend is based on overall increasing warming scores of a group of readings of the core temperature element and the skin temperature element.

64. The system of embodiment 60, wherein the trend is based on decreasing warming scores between readings of the core temperature element and the skin temperature element.

What is claimed is:

1. A temperature monitoring device configured to measure a core temperature and a skin temperature of a patient, the temperature monitoring device comprising:
a flexible substrate, comprising;
a first side surface;
a second side surface;
a center section;
a first tail section extending radially from the center section in a first direction;
a second tail section extending radially from the center section in a second direction; and
a tab section extending radially from the center section in a third direction,
wherein the first tail section is at least partially folded over the center section to form the temperature monitoring device;
an electrical circuit on the first side surface of the flexible substrate, the electrical circuit comprising:
an electrically conductive heater trace, surrounding a central zone at a center of the center section of the flexible substrate;
a first thermal sensor disposed in the central zone;
a second thermal sensor disposed on the first tail section;
a third thermal sensor disposed on the second tail section;
a plurality of electrical pads disposed on the tab section; and
a plurality of conductive traces connecting each of the plurality of electrical pads with one of the first thermal sensor, the second thermal sensor, the third thermal sensor and the heater trace;
a first flexible insulator between the first thermal sensor and the second thermal sensor when the first tail section is folded over the center section; and
a second flexible insulator disposed in the central zone to insulate the first thermal sensor from the heater trace,
wherein the first tail section is folded over the first flexible insulator and the center section to position the first thermal sensor directly over the second thermal sensor in a vertical line drawn through the flexible substrate from the first side surface to the second side surface, with the first flexible insulator located between the first thermal sensor and the second thermal sensor, and
wherein the third thermal sensor is located apart from the first thermal sensor and the second thermal sensor when the first tail section is at least partially folded over the center section, such that the first thermal sensor and the second thermal sensor are arranged to measure the core temperature of the patient and the third thermal sensor is configured to measure the skin temperature of the patient.

2. The temperature monitoring device of claim 1, further comprising multiple heater zones formed by the heater trace, wherein the multiple heater zones are located on the center section of the flexible substrate around the central zone.

3. The temperature monitoring device of claim 1, wherein the plurality of electrical pads comprises five electrical pads configured to slide into and out of connection with a plug of a patient vital signs monitoring system.

4. The temperature monitoring device of claim 3, further comprising a flexible stiffener disposed on the second side surface of the flexible substrate along the tab section and a portion of the center section to support the temperature monitoring device being slid into and out of the plug.

5. The temperature monitoring device of claim 1, further comprising an adhesive on the second side surface of the flexible substrate.

6. The temperature monitoring device of claim 1, further comprising:
   multiple heater zones formed by the heater trace, wherein the multiple heater zones are located on the center section of the flexible substrate around the central zone; and
   multiple slits in the flexible substrate, wherein each of the multiple slits is located between two of the multiple heater zones.

7. The temperature monitoring device of claim 6, wherein a standoff distance between a perimeter of the center section and the third thermal sensor is sufficiently long to thermally isolate the third thermal sensor from the multiple heater zones.

8. The temperature monitoring device of claim 1, wherein a standoff distance between the first thermal sensor and the second thermal sensor is at least twice a radial distance from the first thermal sensor to a perimeter of the center section.

9. The temperature monitoring device of claim 8, wherein the first direction of the first tab is oriented 90 degrees around the center section from the second direction of the second tab and 180 degrees around the center section from the third direction of the tab section.

* * * * *